United States Patent [19]

Nagamatsu

[11] Patent Number: 5,762,070

[45] Date of Patent: Jun. 9, 1998

[54] TREATMENT TOOL FOR ENDOSCOPE, HAVING OPENABLE AND CLOSABLE TREATMENT MEMBERS AND GUIDE MEANS THEREFORE

[75] Inventor: Ryuji Nagamatsu, Hachioji, Japan

[73] Assignee: Olympus Optical Co., Ltd., Tokyo, Japan

[21] Appl. No.: 857,646

[22] Filed: May 16, 1997

Related U.S. Application Data

[63] Continuation of Ser. No. 635,401, Apr. 26, 1996, abandoned.

[30] Foreign Application Priority Data

Apr. 28, 1995 [JP] Japan ................................ 7-106646

[51] Int. Cl.$^6$ ........................... A61B 10/00; A61B 17/28; A61B 5/00
[52] U.S. Cl. ................. 128/751; 606/207; 128/772
[58] Field of Search ........................ 606/1, 35, 39, 606/45–52, 205–211; 128/657, 772; 604/280

[56] References Cited

U.S. PATENT DOCUMENTS

| 4,669,471 | 6/1987 | Hayashi . | |
| 5,217,460 | 6/1993 | Knoepfler | 606/205 |
| 5,281,230 | 1/1994 | Heidmueller | 606/205 |

*Primary Examiner*—Glenn K. Dawson
*Attorney, Agent, or Firm*—Armstrong, Westerman, Hattori, McLeland & Naughton

[57] ABSTRACT

A pair of biopsy cups are provided at a forward-end treatment part of biopsy forceps for an endoscope that are a treatment tool for the endoscope. The pair of biopsy cups are pivoted, by a pin, on a sleeve which is connected to a forward end of a sheath. The pair of biopsy cups are arranged such that cup-shaped forward ends thereof are capable of being opened and closed around the pin. Two through bores are formed in one of the biopsy cups of the forward-end treatment part. One of the through bores is positioned rearwardly more than the other through bore with respect to a major-axis direction. A guide wire for guiding a body of the biopsy forceps for the endoscope is inserted into and passes through the two through bores in a retractable manner.

6 Claims, 6 Drawing Sheets

FIG.4
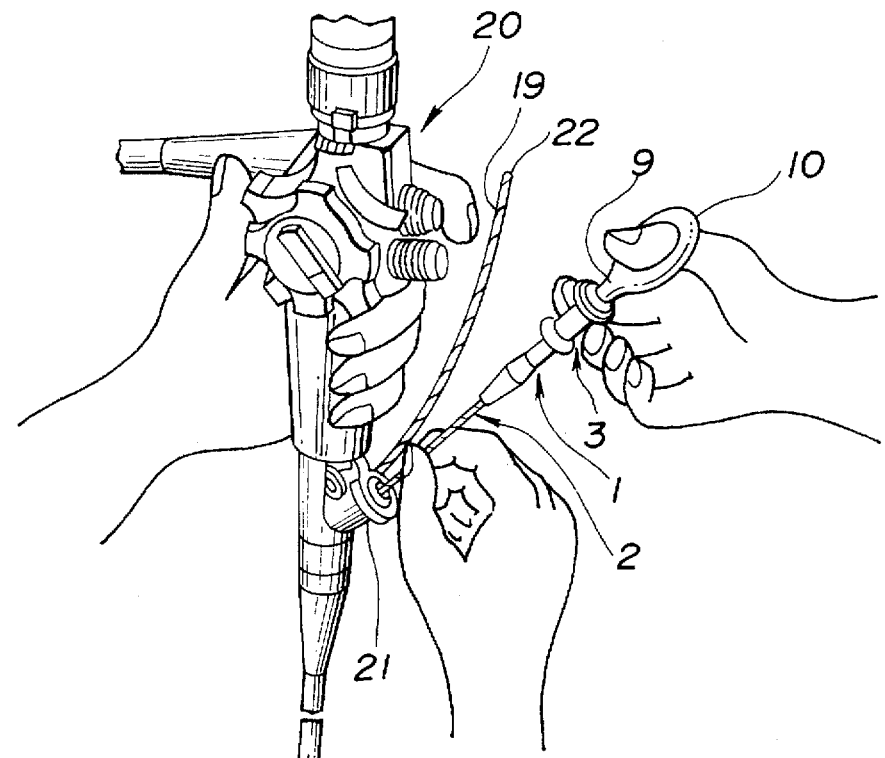
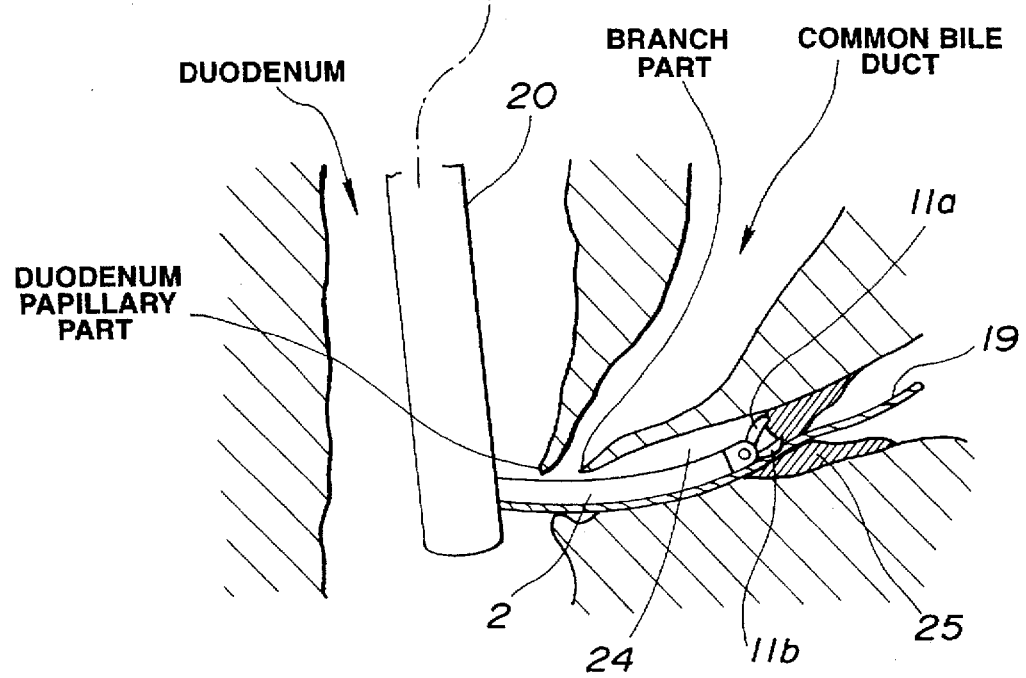
DUODENUM
DUODENUM PAPILLARY PART
BRANCH PART
COMMON BILE DUCT

FIG.5
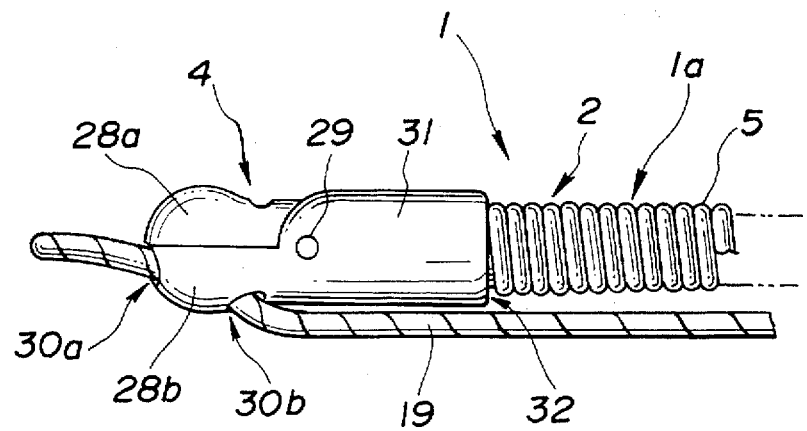
FIG.6(a) FIG.6(b)
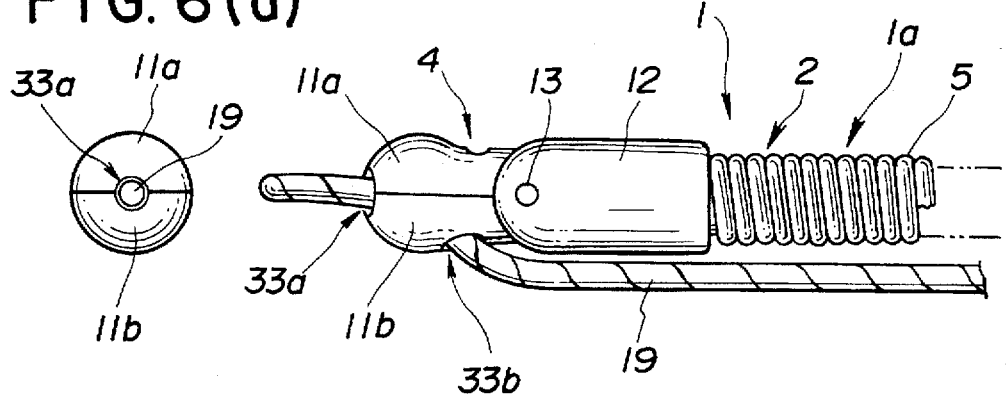
FIG.7(a) FIG.7(b)
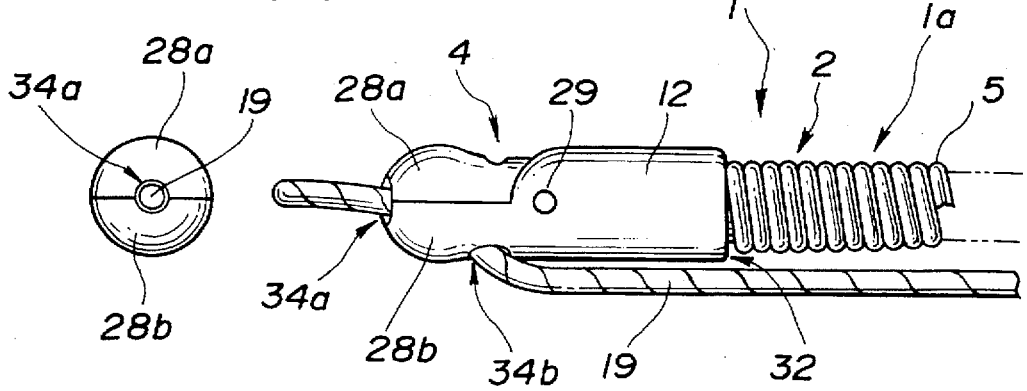

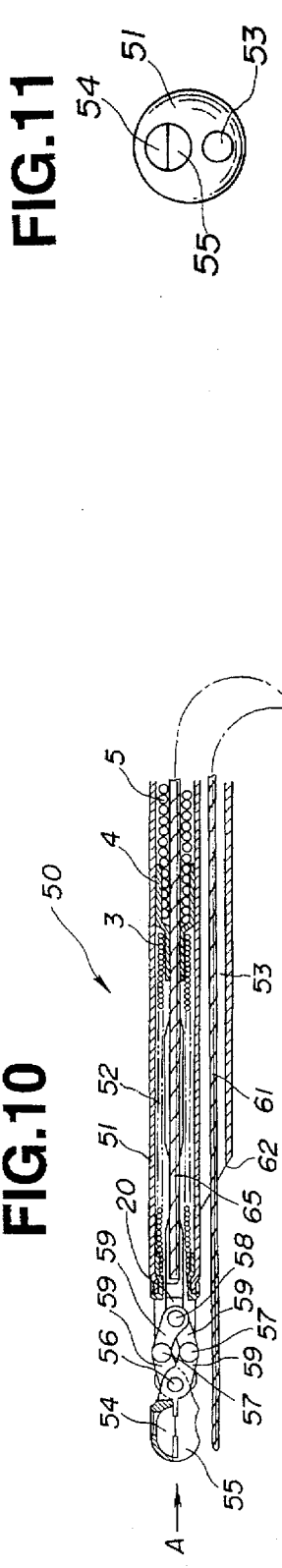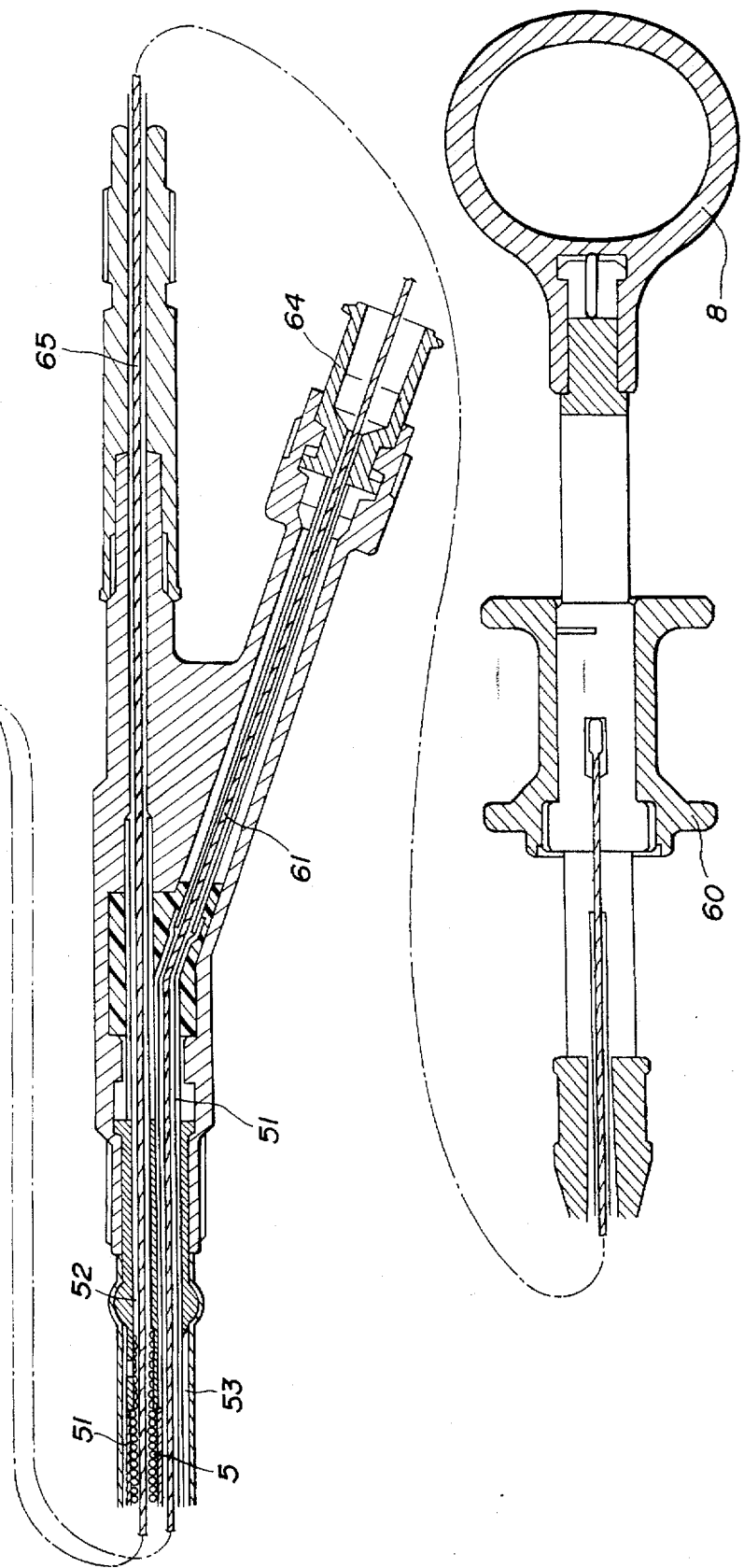

TREATMENT TOOL FOR ENDOSCOPE, HAVING OPENABLE AND CLOSABLE TREATMENT MEMBERS AND GUIDE MEANS THEREFORE

This application is a continuation of application Ser. No. 08/635,401 filed Apr. 26, 1996, now abandoned.

BACKGROUND OF THE INVENTION

1. Field of the Invention

The invention relates to a treatment tool for an endoscope, which is introduced into a body cavity through a channel in the endoscope and which is used to treat affected part of the body.

2. Related Art Statement

In recent years, a treatment tool for an endoscope, which is inserted into an insertion channel in the endoscope, has widely been used in observation treatment under the endoscope.

The treatment tool for the endoscope of this kind, biopsy forceps, for example, is formed by a flexible sheath in the form of a coil, which is inserted into and passes through a treatment-tool insertion and passage channel in the endoscope, a pair of biopsy cups provided through a sleeve which is mounted at a forward end of the flexible sheath, and an operation part which is connected to a rearward end of the flexible sheath, for actuating the biopsy cups through an operation wire and an operation link which are inserted into and pass through the flexible sheath. These biopsy cups, operation link, sleeve, elastic sheath, operation wire and similar are formed, in either case, of a metal, such as, stainless steel or similar, as disclosed in Japanese Patent Unexamined Publication No. 61-247442 (247442/1986).

The arrangement is as follows. That is, upon the use of the biopsy forceps, the insertion part of the endoscope is beforehand inserted into a lacuna. Then, the biopsy forceps are inserted into a treatment-tool insertion and passage channel in the endoscope and are caught within the field of view of the endoscope. Thereafter, a forward-end part of the treatment tool projects into the body cavity so as to be guided into a diseased or affected part, and the pair of biopsy cups which are provided in an openable and closable manner at the forward-end part are operated in opening and closing by the operation part, to thereby take a tissue sample out of the affected part, which occurs at an inner wall of the body cavity.

By the way, as disclosed in Japanese Utility Model Publication No. HEI 6-21449 (21449/1994), in a case where the biopsy forceps or similar are inserted into thin lacuna, for example, into a bile duct and a pancreatic duct, a guide member, for example, a guide wire is inserted into and passes through the treatment-tool insertion and passage channel in the endoscope which is beforehand inserted into the body cavity and, thereafter, the forward-end part of the guide wire projects into the body cavity so as to be guided to an objective part such as the affected part or similar. The arrangement is such that an end part of the guide wire is inserted into a through bore which is provided in the sleeve of the biopsy forceps and, continuously, the biopsy forceps are inserted with the guide wire serving as a guide.

In the above-described conventional or prior-art treatment tool for the endoscope, the arrangement is such that, in a case where it is used together with the guide member, for example, together with the guide wire, the guide wire is inserted into and passes through the through bore which is provided in the sleeve of the forward-end treatment part of the aforesaid treatment tool for the endoscope.

However, there is the following problem. That is, since the sleeve has a bore or hole into and through which the guide wire is inserted and passes, an outer diameter of the treatment part at the forward end of the biopsy forceps for the endoscope increases so that it is difficult to easily insert a particularly thin lacuna, for example, a main pancreatic duct.

Further, there are the following disadvantages or similar. That is, since the guide wire which has a small outer diameter has a used with respect to a part which is particularly narrow lacuna, a resilient or elastic force of the guide wire decreases. In a case where the guide wire is inserted into and passes through the through bore which is provided in the sleeve of the treatment tool for the endoscope, since there is a considerable distance from the through bore to the forward end of the treatment part, it becomes difficult to conform the interval between a path of the guide wire and the insertion path of the forward-end part of the treatment tool for the endoscope, to a generally parallel state so that the forward-end part of the treatment tool for the endoscope is inclined with respect to the insertion path of the guide wire. For this reason, a part of the treatment tool for the endoscope is caught by the inner wall of the body cavity upon passage at a branch point within the body cavity, for example, a branch point between the bile duct and the pancreatic duct, making it difficult to guide the guide wire to the affected part.

Moreover, if the insertion operation of the treatment tool for the endoscope is forcibly executed, a part of the treatment tool for the endoscope is caught by the inner wall surface of the body cavity as described above, and there is a fear that the part of the treatment tool for the endoscope that is caught may stab or poke a hole in the bile duct, the liver, the pancreas and similar.

Furthermore, a case where the forceps are inserted into the narrow lacuna with the guide wire serving as a guide member, a direction of the forceps is oriented toward the same direction as the direction of the guide wire. It is necessary that, if the forceps are pushed, the forward end of the forceps travels in the direction of the guide wire.

However, there is the following problem. That is, in a case of the aforesaid Japanese Utility Model Publication No. HEI 6-21449, if an external force is applied to the guide wire at a proximal end of the through bore, the direction of the guide wire becomes an unexpected or unanticipated direction. Thus, it is impossible to insert the forceps into the thin or fine lacuna into which the guide wire is located.

OBJECT AND SUMMARY OF THE INVENTION

It is an object of the present invention to provide a treatment tool for an endoscope, which can execute guidance safely and certainly with respect to a part which is difficult in insertion operation, like an interior of a narrow lacuna and a complicated branch part, whereby an attempt can be made to improve working efficiency.

According to the invention, there is provided a treatment tool for an endoscope, which has a pair of treatment members at a forward-end part of an insertion part which is inserted into a body cavity. At least one of the treatment members is movable so that the treatment members are openable and closable. A guide means which does not inhibit a guide member for guiding the treatment member to an affected part within the body cavity from being oriented in a direction of the treatment member at the forward-end part.

The guide member is inserted and passes so as not to inhibit the guide member from being oriented in the direction of the treatment member by the guide means at the forward-end part of the treatment tool.

Other features and advantages of the present invention will sufficiently become apparent from the following explanation.

BRIEF DESCRIPTION OF THE DRAWINGS

FIGS. 1 to 7(a) and (b) relate to a first embodiment of the invention, FIG. 1 being a partial side elevational view showing an arrangement of the biopsy forceps for an endoscope of the presentation;

FIG. 2 is a partial side elevational view showing an arrangement of a rearward end of the biopsy forceps for the endoscope in FIG. 1;

FIG. 3 is an enlarged partial side view showing an arrangement of a principal part of a forward end of the biopsy forceps for the endoscope in FIG. 1;

FIG. 4 is a perspective view illustrating the function at the time the biopsy forceps for the endoscope in FIG. 1 is inserted into and passes through the endoscope and is practically used;

FIG. 5 is a partial side elevational view showing an arrangement of a first modification of the biopsy forceps for the endoscope in FIG. 1;

FIG. 6(a) and 6(b) are partial front and left-hand side elevational views showing an arrangement of a second modification of the biopsy forceps for the endoscope in FIG. 1;

FIG. 7(a) and 7(b) are partial front and left-hand side elevational views showing an arrangement of a third modification of the biopsy forceps for the endoscope in FIG. 1;

FIG. 9 is a partial side elevational view showing an arrangement of a modification of the biopsy forceps for the endoscope in FIG. 8;

FIGS. 10 and 11 relate to a third embodiment of the invention, FIG. 10 being an exploded side elevational view showing an arrangement of the biopsy forceps for an endoscope; and FIG. 11 is a front view showing an arrangement of a forward-end surface of the biopsy forceps for the endoscope in FIG. 10.

DETAILED DESCRIPTION OF THE PREFERRED EMBODIMENTS

Concrete or specific embodiments of the invention will hereunder be described.

Figure 1:
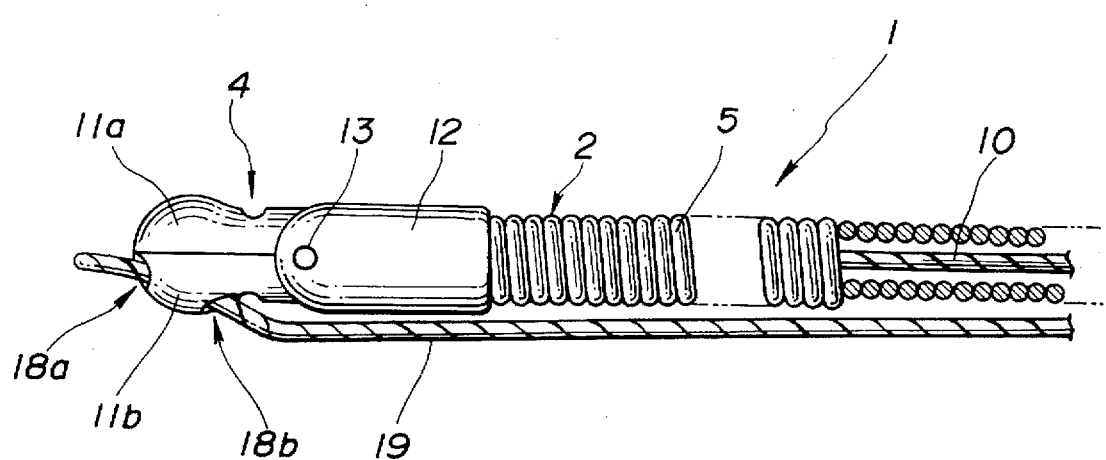

As shown in FIG. 1, a sheath 2 having resiliency or elasticity is provided on the side of a forward end of biopsy forceps 1 for an endoscope, for example, which is a treatment tool for the endoscope according to a first embodiment. The sheath 2 has a proximal-end part thereof which is provided with an operation part 3. Further, a forward-end treatment part 4 is provided at the forward-end part of the sheath 2. Moreover, the sheath 2 is formed by a tight wound coil 5 in which a wire made of stainless steel, for example, is tightly wound.

Figure 2:
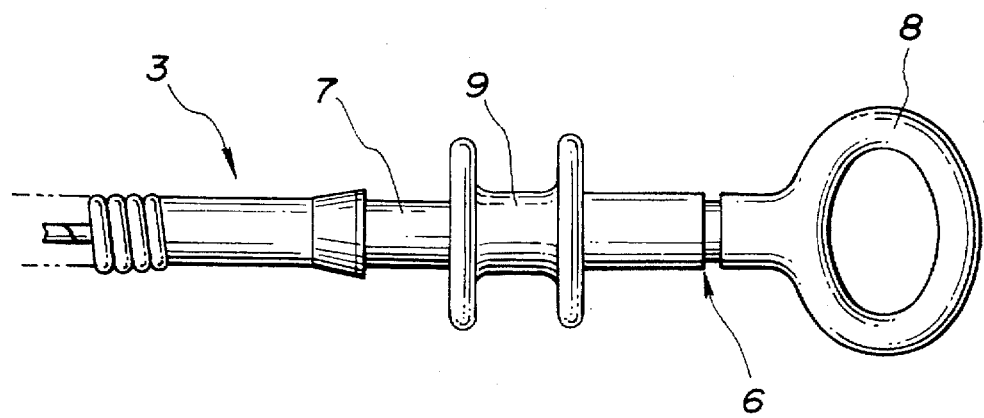

The sheath 2 has a rearward end thereof which is connected to an operation part body 6 of the operation part 3, as shown in FIG. 2. The operation part body 6 is formed by a shank 7 and a finger-hanging ring 8 which is formed at a rearward end part of the shank 7. Moreover, a slider 9 is loosely fitted over the shank 7. The stranded operation wire 10 has a rearward end thereof which is connected to the slider 9.

Returning to FIG. 1, on one hand, a pair of biopsy cups 11a and 11b are provided at the forward-end treatment part 4. These biopsy cups 11a and 11b are pivoted, by a pin 13, on a sheath 12 which is connected to the forward end of the sheath 2. These biopsy cups 11a and 11b are arranged such that cup-like forward ends thereof are openable and closable around the pin 13.

Figure 3:
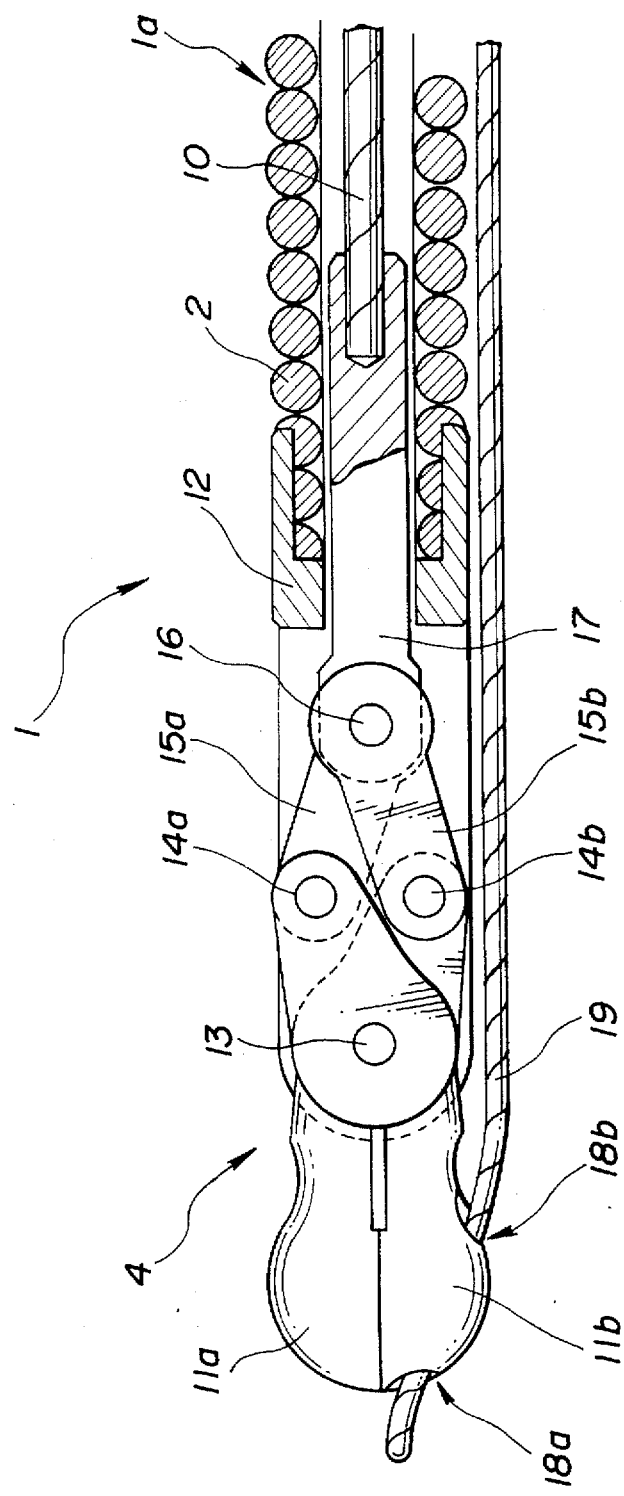

Furthermore, as shown in FIG. 3, the biopsy cups 11a and 11b have respective proximal end parts thereof which are mounted to first ends of operation links 15a and 15b by pins 14a and 14b. These operation links 15a and 15b have respective second opposite ends thereof which are mounted to a connection member 17 by a pin 16. The operation wire 10 which is inserted into and passes through the sheath 2 has a forward end thereof which is connected to the connection member 17 and is led toward the side of the operation part 3.

Further, through bores 18a and 18b are formed in the biopsy cup 11b of the forward-end treatment part 4. The through bore 18b is positioned more rearward than the through bore 18a with respect to a longitudinal or major-axis direction. Moreover, the arrangement is such that a guide member for guiding a body 1a of the biopsy forceps 1 for the endoscope, for example, a guide wire 19 is inserted into and passes through these through bores 18a and 18b in a retractable manner.

Operation of the embodiment which is arranged in this manner will be described.

FIG. 4 shows an example at the time the body 1a of the biopsy forceps 1 for the endoscope is inserted into and passes through an endoscope 20, and the biopsy forceps 1 is used practically.

Upon the use of the biopsy forceps 1 for the endoscope, the guide wire 19 is inserted into and passes through a channel 21 in the endoscope 20 which is beforehand inserted into the organism atrium or cavity prior to the body 1a of the biopsy forceps 1 for the endoscope. The forward-end part of the guide wire 19 projects into the body cavity, and is guided to the affected part or similar, for example, to an objective part 25 of a main pancreatic duct 24. In this case, since the guide wire 19 is thin as compared with an outer diameter size of a general treatment tool (on the order of 1.7~3 mm of an outer diameter, for example as compared to the fact that a diameter is equal to or less than 0.9 mm, for example), it is possible to safely and surely insert the guide wire 19 also into a part which is difficult for insertion operation, like an interior of a thin lacuna such as a respiratory system, a bile duct, a pancreatic duct or similar. The guide wire 19 is guided to the objective part 25 and, thereafter, a distal-end part 22 of the guide wire 19 is inserted into and passes through the through bores 18a and 18b which are provided in the biopsy cup 11b. Continuously, the body 1a of the biopsy forceps 1 for the endoscope is inserted to the objective part 25 with the guide wire 19 serving as the guide.

Further, the body 1a of the biopsy forceps 1 for the endoscope is inserted into the objective part 25 and, thereafter, the slider 9 which is provided on the operation part body 6 slides, to execute biopsy of an organism tissue or similar by opening and closing operation of the biopsy cups 11a and 11b. Thereupon, it is also possible to remove the guide wire 19 to the outside of the body cavity and, thereafter, to execute a biopsy, while the body 1a of the biopsy forceps 1 for the endoscope is left at the objective part 25.

After biopsy, the body 1a of the biopsy forceps 1 for the endoscope is removed from the endoscope 20 while the guide wire 19 is left at the objective part 25 such that it is possible to insert the subsequently inserted treatment tool or similar into the objective part 25 easily and for a short period of time. Moreover, it is also possible to remove the body 1a of the biopsy forceps 1 for the endoscope from the endoscope 20, together with the guide wire 19.

In this manner, according to the present embodiment, it is possible to reduce the outer diameter of the forward-end treatment part 4, and it is possible to insert the biopsy forceps 1 for the endoscope with the guide wire 19 which was provisionally inserted into the objective part serving as the guide. Furthermore, since the guide wire 19 can directly guide the biopsy cups 11a and 11b, it is possible to insert the body 1a of the biopsy forceps 1 for the endoscope to the objective part safely and reliably without the forward-end treatment tool 4 of the biopsy forceps 1 for the endoscope being caught by the wall of the body cavity in a small opening, for example, a duodenum papillary part and a complicated branch part, for example, a branch between the bile duct and the pancreatic duct, a branch between the left and the right bile ducts or a branch part of the respiratory system. Accordingly, since the body 1a of the biopsy forceps 1 for the endoscope can be guided safely and reliably as compared with a conventional or prior-art one, it is possible that an attempt is made to improve the operation efficiency of the insertion operation of the body 1a of the biopsy forceps 1 for the endoscope.

In connection with the above, it has been described that the biopsy forceps 1 for the endoscope is formed or arranged as shown in FIGS. 1 and 3. However, the present invention should not be limited to this. The invention may be arranged like first to third modifications shown in the following FIGS. 5 to 7.

(First Modification)

As shown in FIG. 5, the forward-end treatment part 4 of the body 1a of the biopsy forceps 1 for the endoscope is made to a single swinging type or a simple type, and is fixed to the forward end of the sheath 2. The forward-end treatment part 4 may be formed by a proximal part 32 which has a pair of support pieces 31, a fixed biopsy cup 28b which is provided between the support pieces 31 and which is fixed with respect to the proximal part 32, and a movable biopsy cup 28a which is movable with respect to the proximal part 32.

In such first modification, an unshown arm part, for example, is provided to project from the proximal end of the movable biopsy cup 28a. The arm part has a proximal end thereof to which one end of an unshown operation wire is connected through, for example, an unshown link mechanism. Moreover, the arm part has a middle part thereof which is pivoted for angular movement by the pin 29 with respect to the support piece 31. Furthermore, the fixed biopsy cup 28b of the forward-end treatment part 4 is formed therein with through bores 30a and 30b. The through bore 30b is positioned rearwardly more than the through bore 30a with respect to the major-axis direction. Further, the arrangement is such that the guide member for guiding the body 1a of the biopsy forceps 1 for the endoscope, for example, the guide wire is inserted into and passes through these through bores 30a and 30b in a retractable manner. The first modification is arranged in this manner. Thus, the first modification can obtain function and advantages similar to those of the first embodiment.

(Second Modification)

Moreover, as shown in FIG. 6, a through bore 33a is provided on a contact surface between the biopsy cups 11a and 11b of the forward-end treatment part 4 of the body 1a of the biopsy forceps 1 for the endoscope, while a through bore 33b is provided in the biopsy cup 11b. The through bore 33b may be so arranged as to be positioned rearwardly more than the through bore 33a with respect to the major-axis direction. Furthermore, the present second modification is arranged such that the guide wire 19 for guiding the body 1a of the biopsy forceps 1 for the endoscope is inserted into and passes through the through bores 33a and 33b in a retractable manner. Because the second modification is arranged in this manner, the second modification can obtain function and advantages which are similar to those of the first embodiment.

(Third Modification)

Further, the first modification is applied to the second modification, whereby, as shown in FIG. 7, if the arrangement is such that a through bore 34a is provided in the contact surfaces of the pair of biopsy cups 28a and 28b, in which the forward-end treatment part 4 is of single swinging type, of the body 1a of the biopsy forceps 1 for the endoscope, and a through bore 34b is provided in any one of biopsy cups, for example, in the fixed biopsy cup 28b, it is possible to obtain function and advantages similar to those of the first embodiment.

A second embodiment will subsequently be described. Since the second embodiment is almost the same as the first embodiment, only different arrangements will be described.

Figure 8:
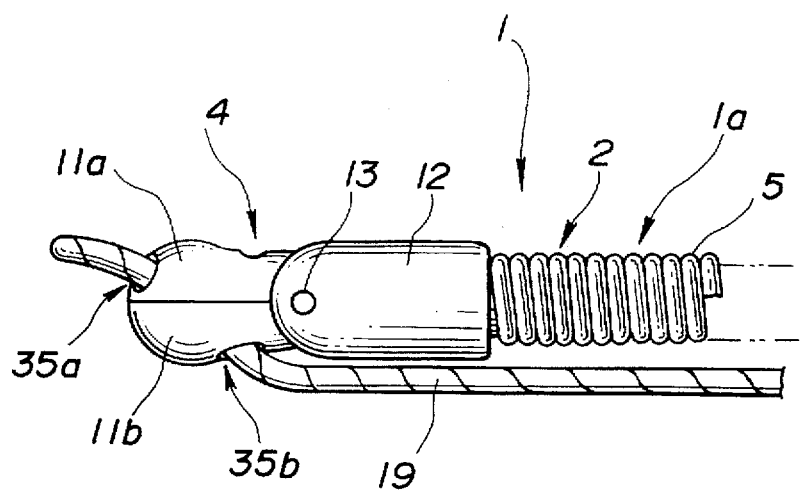
FIGS. 8 and 9 relate to a second embodiment of the invention, FIG. 8 being a partial side elevational view showing an arrangement of biopsy forceps for the endoscope in FIG. 1.

In the second embodiment, as shown in FIG. 8, the biopsy cup 11a of the forward-end treatment part 4 of the body 1a of the biopsy forceps for the endoscope is provided therein with a through bore 35a, while the biopsy cup 11b is provided therein with a through bore 35b. The through bore 35b is positioned rearwardly more than the through bore 35a with respect to the major-axis direction. Moreover, the arrangement is such that the guide wire 19 for guiding the body 1a of the biopsy forceps 1 for the endoscope is inserted into and passes through the through bores 35a and 35b in a retractable manner.

Figure 9:
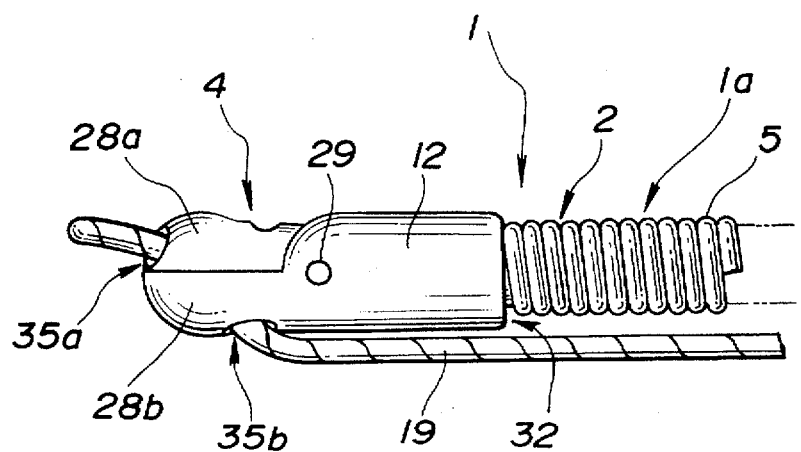

In connection with the above, as shown in FIG. 9, the through bores 35a and 35b may be provided respectively in the pair of organism cups 28a and 28b in which the forward-end treatment part 4 of the body 1a of the biopsy forceps for the endoscope is of single swinging type, like that as shown in the first modification of the first embodiment.

The other arrangement and functions are the same as those of the first embodiment.

Accordingly, since the present embodiment is provided with the through bores respectively in the pair of biopsy cups, it is possible to further reduce the outer diameter of the biopsy cups, particularly, it is possible to insert the biopsy forceps 1 for the endoscope further easily even in a part which has a narrow in lacuna, addition to the advantages of the first embodiment.

A third embodiment will subsequently be described. Since the third embodiment is almost the same as the first embodiment, only different arrangements will be described.

The third embodiment is an embodiment of organism forceps in which a lacuna or guide tube 53 into which the guide wire 61 is capable of being inserted is juxtaposed against the insertion part or the forward-end of the treatment tool, and the lacuna or guide tube 53 can be inserted into a bile duct, a pancreatic duct or similar through the guide wire 61, so that an attempt can be made to simplify the treatment operation and shorten the treatment time.

Specifically, in biopsy forceps 50 according to the third embodiment, as shown in FIG. 10, two lacunae 52 and 53 are juxtaposed against each other in a tube 51 over the side of the rearward end thereof from the side of the forward end thereof. As shown in FIG. 11 which is viewed from an arrow A in FIG. 10, biopsy cups 54 and 55 are provided on the side of the forward end in the lacuna 52 of the two lacunae. Returning to FIG. 10, these biopsy cups 54 and 55 form a link mechanism by a fixed pin 56, slide pins 57 and 58 and a link 59.

The link mechanism is so arranged as to be able to execute remote control or operation by a slider 60 of the operation part on a side of the treatment tool where an operator would put his hand, through the operation wire 65. Specifically, the arrangement is such that, in a case where the organism forceps 50 are inserted into the endoscope, to execute a biopsy of a mucous membrane or similar within the body cavity, the link mechanism at the forward-end part is operated or actuated by sliding operation of the slider 60 which is provided on a side of the treatment tool where an operator would put his hand, and the opening and closing operation of the biopsy cups 54 and 55 is executed, whereby biopsy of a tissue piece or similar can be executed or made.

Moreover, a guide wire 61 can be so arranged as to be inserted into and to pass through the other lacuna 53. The lacuna 53 is juxtaposed against the lacuna 52 from a forward-end part 62 to a branch part 63, and passes through or penetrates from the branch part 63 to a mouth ring or a base 64.

In the third embodiment shown in FIG. 10, the guide means is a guide tube which is juxtaposed against the treatment tool from a vicinity of the treatment members to a vicinity on the rearward end of the operation wire which is provided with the treatment members at the other end thereof.

Subsequently, a case where the organism forceps 50 according to the present embodiment is used in combination with the guide wire will be described concretely or specifically.

Generally, it is said that it is extremely difficult to insert the treatment tool into the bile duct and the pancreatic duct through the channel in the endoscope. For this reason, a technique has generally been executed in which the guide wire is once inserted into the bile duct/the pancreatic duct, and the treatment tool or the like is inserted along the guide wire (in this connection, since the endoscope for the bile duct/the pancreatic duct or similar executes, at once, various diagnosis and medical treatments, there are many cases where several kinds of different treatment tools are used. Accordingly, repeating of insertion and re-insertion is frequently executed).

For example, in a case where the guide wire has already been inserted into the bile duct or the pancreatic duct, the guide wire 61 is inserted into and passes through the forward-end part 62 of the lacuna 53 of the organism forceps 50, and the organism forceps 50 are inserted into the endoscope →the duodenum papillary part →the bile duct or the pancreatic duct along the guide wire 61. After insertion, as described above, biopsy is executed by slide operation on a side of the treatment tool where an operator would put his hand.

After biopsy, if the organism forceps 50 are removed, while the guide wire 61 is left in the bile duct or the pancreatic duct, insertion of the treatment tool can quickly be executed in a case where the next treatment is executed.

In this manner, the guide wire 61 is used whereby it is possible to easily insert the organism forceps 50 according to the embodiment into the bile duct or the pancreatic duct. Moreover, since the invention is arranged such that the two lacunae 52 and 53 are juxtaposed against each other, and the biopsy part and the insertion and passage part of the guide wire do not interfere with each other, a biopsy can be executed while the guide wire is left in the body cavity. Thus, an attempt can be made to reduce treatment time.

In connection with the above, the forward-end part 62 may be cut obliquely with respect to the major-axis direction. By doing so, insertion from the duodenum papillary part to similar bile duct, the pancreatic duct or the can further easily be executed.

In connection with the above, the present invention is not limited to each of the above-described embodiments. For example, in each of the aforesaid embodiments, a case where the invention is applied to the biopsy forceps is indicated. However, the invention may also be applied to grasping or gripping forceps or similar. Furthermore, the above-described embodiments can be variously modified and carried into practice without deviating from the scope of the present invention.

In this invention, it is apparent that widely differing working modes can be formed on the basis of this invention without departing from the spirit and scope of the invention. This invention is not restricted by any specific embodiments, except as limited by the appended claims.

What is claimed is:

1. A treatment tool for an endoscope, comprising:

an insertion part which is insertable into said endoscope;

a pair of treatment members having a forward-end part and being located at a forward-end part of said insertion part, wherein at least one of said pair of treatment members is movable so that said pair of treatment members are openable and closable with respect to each other;

a guide member;

a guide means for guiding said guide member so that said forward-end part of said treatment members does not prevent said guide member from orienting in a direction towards said treatment members, wherein said guide member guides said treatment members to an area to be treated by said treatment members within said body cavity;

wherein said guide means is a through bore which is provided in any one of either a first treatment member or a second treatment member of said pair of treatment members, or in both said first treatment member and said second treatment member; and wherein said through bore has first and second openings into and through which said guide member, which is a guide wire that guides said treatment members to an area to be treated by said treatment members within said body cavity, can be inserted and pass in a retractable manner.

2. The treatment tool for an endoscope, according to claim 1, wherein said first and second openings are both provided on either one of a first treatment member or a second treatment member of said pair of treatment members.

3. The treatment tool for an endoscope, according to claim 1, wherein said first and second openings are provided in a first treatment member and a second treatment member, respectively, of said pair of treatment members.

4. The treatment tool for an endoscope, according to claim 1, wherein either one of said first and second openings is an opening on a side of a forward end of one of said treatment members and is provided through a surface in which a first of said pair of treatment members contacts a second of said pair of treatment members.

5. A treatment tool for an endoscope, comprising:

an insertion part which is insertable into said endoscope;

a pair of treatment members having a forward-end part and being located at a forward-end part of said insertion part, wherein at least one of said pair of treatment members is movable so that said pair of treatment members are openable and closable with respect to each other;

a guide member, wherein said guide member is a guide wire that guides said pair of treatment members to an area within a body cavity to be treated by said treatment members; and a guide means for guiding said guide member so that said forward-end part of said treatment members does not prevent said guide member from orienting in a direction towards said treatment members, wherein said guide means is a hollow guide tube which houses said guide member and which is located to one side of and is juxtaposed against a main hollow tube portion of said treatment tool from adjacent said treatment members to adjacent a proximal end of said treatment tool.

6. The treatment tool for an endoscope, according to claim 5, wherein said guide tube has a forward end part thereof which is formed obliquely with respect to a main longitudinal axis of said treatment tool.

\* \* \* \* \*